US010165993B2

(12) United States Patent
Kim et al.

(10) Patent No.: US 10,165,993 B2
(45) Date of Patent: Jan. 1, 2019

(54) X-RAY IMAGIN DEVICE WITH DISTRIBUTED X-RAY SOURCE

(71) Applicants: VATECH Co., Ltd., Gyeonggi-do (KR); VATECH EWOO Holdings Co., Ltd., Gyeonggi-do (KR)

(72) Inventors: Tae Woo Kim, Gyeonggi-do (KR); Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 176 days.

(21) Appl. No.: 15/117,445

(22) PCT Filed: Feb. 9, 2015

(86) PCT No.: PCT/KR2015/001276
§ 371 (c)(1),
(2) Date: Aug. 8, 2016

(87) PCT Pub. No.: WO2015/119466
PCT Pub. Date: Aug. 13, 2015

(65) Prior Publication Data
US 2016/0345919 A1 Dec. 1, 2016

(30) Foreign Application Priority Data
Feb. 7, 2014 (KR) .................. 10-2014-0014024

(51) Int. Cl.
*H01L 27/146* (2006.01)
*A61B 6/00* (2006.01)

(52) U.S. Cl.
CPC .......... *A61B 6/4266* (2013.01); *A61B 6/4007* (2013.01); *A61B 6/4014* (2013.01);
(Continued)

(58) Field of Classification Search
CPC .... A61B 6/00; A61B 6/14; A61B 6/40; A61B 6/4007; A61B 6/4014; A61B 6/4021;
(Continued)

(56) References Cited

U.S. PATENT DOCUMENTS 4,349,740 A * 9/1982 Grassmann .............. A61B 6/02
378/134
8,837,669 B2 * 9/2014 Morton .................. A61B 6/022
378/41
(Continued)

FOREIGN PATENT DOCUMENTS

DE 102010040308 A1 3/2012
JP 2005-177469 A 7/2005
(Continued)

OTHER PUBLICATIONS

European Patent Office, Opinion and Supplementary European Search Report of corresponding EP Patent Application No. 15746575.8, dated Nov. 8, 2017.

*Primary Examiner* — Anastasia Midkiff
(74) *Attorney, Agent, or Firm* — IP Legal Services, LLC

(57) ABSTRACT

The present invention relates to an X-ray imaging device and, particularly, to an X-ray imaging device which is formed by pixelating a plurality of X-ray emitting elements for respectively emitting X-rays toward an object to be photographed and a plurality of X-ray detecting elements for respectively detecting X-rays passing through the object to be photographed, on the same or different flat surfaces or curved surfaces in a matrix.

13 Claims, 6 Drawing Sheets

(52) U.S. Cl.
CPC ............. *H01L 27/14618* (2013.01); *A61B 2560/0406* (2013.01); *A61B 2562/164* (2013.01)

(58) Field of Classification Search
CPC ....... A61B 6/4028; A61B 6/42; A61B 6/4208; A61B 6/4233; A61B 6/4266; A61B 6/4275; A61B 6/44; A61B 6/4429; A61B 6/4435; A61B 6/50; A61B 6/501; A61B 6/587; A61B 2560/00; A61B 2560/0406; A61B 2560/0462; A61B 2562/00; A61B 2562/04; A61B 2562/043; A61B 2562/046; A61B 2562/16; A61B 2562/164; A61B 2562/166; H01L 27/144; H01L 27/1446; H01L 27/146; H01L 27/14601; H01L 27/14603; H01L 27/14618; H01L 27/148; H01L 27/14806; H01L 27/14812; H01J 35/00; H01J 35/02; H01J 35/025; H01J 35/16; H01J 37/00; H01J 37/02; H01J 37/16; H01J 37/22; H01J 37/244; H01J 2235/00; H01J 2235/16; H01J 2235/163; H01J 2893/003; H01J 2893/007; H01J 2237/00; H01J 2237/02; H01J 2237/06; H01J 2237/061; H01J 2237/063; H01J 2237/06341; H01J 2237/15; H01J 2237/16; H01J 2237/244; H01J 2237/24415; H01J 2237/24465; H01J 2237/2485; H01J 2237/2487; H01J 2237/248; H05G 1/00; H05G 1/02; H05G 1/04; H05G 1/52; H05G 1/70; G91N 2223/00; G91N 2223/03; G91N 2223/04; G91N 2223/20; G91N 2223/30; G91N 2223/306; G91N 2223/308; G91N 2223/33; G91N 2223/335; G91N 2223/40; G91N 2223/413; G91N 2223/427; G91N 2223/50; G91N 2223/501; G91N 2223/5015; G91N 2223/612; G91N 2223/612
See application file for complete search history.

(56) References Cited

U.S. PATENT DOCUMENTS

| | | | |
|---|---|---|---|
| 2005/0111610 A1 | 5/2005 | De Man et al. | |
| 2005/0226364 A1 | 10/2005 | Bernard De Man et al. | |
| 2006/0008047 A1* | 1/2006 | Zhou | A61B 6/032 378/10 |
| 2007/0237296 A1* | 10/2007 | Wyatt | A61L 2/082 378/64 |
| 2010/0266097 A1* | 10/2010 | Okunuki | A61B 6/032 378/9 |
| 2014/0023178 A1* | 1/2014 | Kim | G01N 23/04 378/62 |
| 2014/0146942 A1 | 5/2014 | Tahtali | |

FOREIGN PATENT DOCUMENTS

| | | |
|---|---|---|
| JP | 2005-288152 A | 10/2005 |
| JP | 2009-153589 A | 7/2009 |
| KR | 10-2014-0013403 A | 2/2014 |
| WO | 2009/115982 A1 | 9/2009 |
| WO | 2012/155201 A1 | 11/2012 |

\* cited by examiner

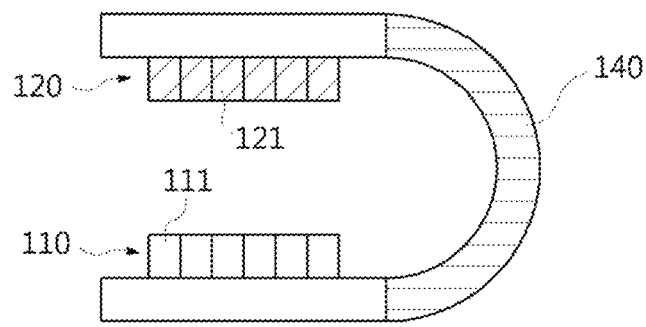

X-RAY IMAGIN DEVICE WITH DISTRIBUTED X-RAY SOURCE

CROSS REFERENCE TO RELATED APPLICATIONS

This application is a National Stage Patent Application of PCT International Patent Application No. PCT/KR2015/001276 (filed on Feb 9, 2015) under 35 U.S.C. § 371, which claims priority to Korean Patent Application No. 10-2014-0014024 (filed on Feb. 7, 2014), the teachings of which are incorporated herein in their entireties by reference.

TECHNICAL FIELD

The present invention relates generally to an X-ray radiography device. More particularly, the present invention relates to an X-ray radiography device in which a plurality of X-ray emitting elements emit X-rays to a target and a plurality of X-ray detecting elements detect X-rays transmitted through the target, whereby the X-ray emitting elements and the X-ray detecting elements are arranged in a pixel matrix on a same or separate surface that is either planar or curved.

BACKGROUND ART

Generally, X-rays decrease according to an X-ray attenuation coefficient of a target that is placed within X-ray beam paths, and the coefficient may be varied by a photoelectric effect, Compton scattering, etc.

An X-ray radiography device is a radiograph imaging device that obtains a two-dimensional (2D) projection image or a three-dimensional (3D) computed tomography image by using a characteristic of X-rays that penetrates a target, and the device includes an X-ray generator that emits X-rays and an X-ray detector that detects X-rays.

The X-ray generator includes a vacuum tube in which cathodes and anodes are provided and sealed. X-rays are generated by colliding heat electrodes that are emitted from cathodes by high power with a target of anodes. Herein, the X-rays generated from the X-ray generator are emitted in a sine wave according to an angle of the target. Thus, conventional X-ray generators include a collimator that controls an irradiation shape of the X-rays to a proper size such as cone beam size or fan beam size according to the size of the target or a radiograph purpose.

The X-ray detector includes a plurality of X-ray detecting elements arranged in a two dimensional matrix on a planar surface. Each of the X-ray detecting elements generates an electric signal that is proportional to an amount of incident X-rays on the X-ray detecting elements. Herein, conventional X-ray detectors include a signal processing circuit that generates projection data of the target by using electrical signals and positional information of each X-ray detecting element.

FIG.1 is a view showing an X-ray radiography device using a cone beam X-ray that is mainly used in dental clinics.

Referring to FIG. 1, the X-ray radiography device generally includes an X-ray generator 1 and an X-ray detector 2 that face each other with a target 3 interposed between the X-ray generator 1 and the X-ray detector 2.

X-rays generated from the X-ray generator 1 diffuse in a cone beam shape, transmit through the target 3 and are incident on the X-ray detector 2. X-ray detecting elements of the X-ray detector 2 generate electrical signals that are proportional to an amount of incident X-rays on the X-ray detecting elements. Therefore, the X-ray detector 2 may obtain an interior 2D projection image 4 of the target 3 by image processing projection data that are obtained by the electrical signals and positional information of the X-ray detecting elements. Further, a 3D computed tomography image of the target 3 may be obtained by reconstructing multi-directional projection data that are obtained by rotating the X-ray generator 1 and the X-ray detector 2.

Meanwhile, in a conventional X-ray radiography device, X-rays generated from the X-ray generator 1 diffuse in a cone shaped beam or a fan shaped beam, thus, a source to detector distance (SDD) between the X-ray generator 1 and the X-ray detector 2 may be secured to radiograph a target 3 having more than a predetermined size. In addition, the X-ray detector 2 having a wider or larger surface than the target 3 is required.

Accordingly, it is problematic in that size and manufacturing cost of an X-ray radiography device are increased. Further, image distortion such as geometric penumbra occurs within a radiograph.

DISCLOSURE OF INVENTION

Technical Problem

As a result of efforts to reduce the size of an X-ray radiography device and minimize image distortion of a radiograph, the inventors have completed the present invention by developing a technical configuration of the X-ray radiography device.

Therefore, an object of the present invention is to provide an X-ray radiography device that is decreased in size, has a minimized X-ray detector area, and has reduced image distortion.

The objects of the present invention are not limited to the above-mentioned objects, and other unmentioned objects thereof will be clearly understood by those skilled in the art from the following descriptions.

Technical Solution

In order to achieve the above object, according to one aspect of the present invention, there is provided an X-ray radiography device, the device includes: an X-ray source including a plurality of X-ray emitting elements arranged in at least 2×2 pixel matrix on a planar surface or a curved surface and respectively emitting X-rays to a target; and an X-ray detector detecting the X-rays transmitted through the target.

In a preferred embodiment, the X-ray detector may include a plurality of X-ray detecting elements arranged in an at least 2×2 pixel matrix on a planar surface or a curved surface to be mapped one-to-one or one-to-many to the X-ray source, and respectively to detect each of the X-rays transmitted through the target.

In a preferred embodiment, the X-ray emitting elements may include cathodes of carbon nanotubes.

In a preferred embodiment, the plurality of X-ray emitting elements and the plurality of X-ray detecting elements may be arranged on separate planar surfaces or on separate curved surfaces.

In a preferred embodiment, the X-ray emitting elements and the X-ray detecting elements may be arranged to face each other with the target being interposed between the X-ray emitting elements and the X-ray detecting elements.

In a preferred embodiment, the X-ray radiography device may further include a flexible bending part connecting the separate planar surfaces or the separate curved surfaces to each other.

In a preferred embodiment, one of the plurality of X-ray emitting elements and the plurality of X-ray detecting elements may be arranged along a curved surface having an arc-shaped cross-section perpendicular to a vertical axis of the target to cover at least three sides of the target, and a remaining one of the plurality of X-ray emitting elements and the plurality of X-ray detecting elements may move with facing the target while being interposed between the target and the remaining one of the plurality of X-ray emitting elements and the plurality of X-ray detecting elements.

In a preferred embodiment, the X-ray emitting elements and the X-ray detecting elements may be arranged on a same planar surface or a same curved surface.

In a preferred embodiment, the X-ray emitting elements and the X-ray detecting elements may be arranged in a grid matrix to alternately dispose the X-ray emitting elements and the X-ray detecting elements in each column and each row, or in a stripe matrix to respectively dispose the X-ray emitting elements and the X-ray detecting elements are disposed in alternate columns or in alternate rows.

In a preferred embodiment, the planar surface or the curved surface may have flexibility.

In a preferred embodiment, the X-ray emitting elements may sequentially emit the X-rays in a row or a column.

Advantageous Effects

The present invention has outstanding effects as follows.

The X-ray radiography device according to the present invention provides an X-ray source including: a plurality of X-ray emitting elements, the X-ray emitting elements being arranged in a pixel matrix and respectively emitting X-rays to a part or the entirety of a target; and an X-ray detector including a plurality of X-ray detecting elements, the X-ray detecting elements being arranged in a pixel matrix, being mapped one-to-one or one-to-many to the X-ray emitting elements, and respectively detecting the X-rays transmitted through the part or the entirety of the target.

As a result, 2D or 3D images of the target are obtained by using X-rays that are actually focused in parallel, thus, a source to detector distance (SDD) between the X-ray generator and the X-ray detector and image distortion may be minimized.

In addition, the X-ray radiography device according to the embodiment of the present invention may obtain a 3D image without physically moving the X-ray source or the X-ray detector, or both of the X-ray source and the X-ray detector by arranging the X-ray emitting elements of the X-ray source and the X-ray detecting elements of the X-ray detector on the same or separate surfaces that are planar or curved surfaces.

Therefore, the X-ray radiography device according to the embodiment of the present invention provides effect of minimizing the size and simplifying the configuration thereof by simplifying a driving mechanism.

BRIEF DESCRIPTION OF DRAWINGS

FIG. 6 is a view showing an X-ray radiography device according to a third embodiment of the present invention.

FIGS. 7a, 7b, 8a and 8b are schematic views of the X-ray source and the X-ray detector of an X-ray radiography device according to a fourth embodiment of the present invention.

NUMERALS

Figure 1:
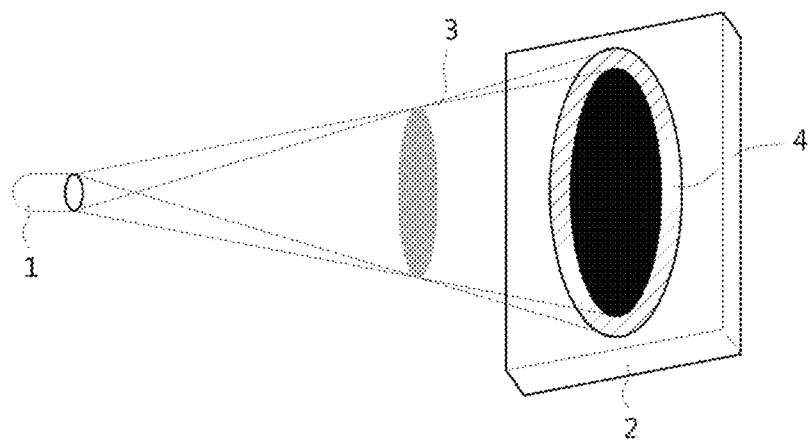
FIG. 1 is a view showing an X-ray radiography device using a cone beam type X-ray that is mainly used in dental clinics.

110: X-ray source
111: X-ray emitting element
120: Detector
121: X-ray detecting element
130: Housing
140: Bending part

BEST MODE FOR CARRYING OUT THE INVENTION

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant. In this case, the meaning of the selected terms will be described in the detailed description. Thus, the terms used herein have to be defined based on the meaning of the terms together with the description throughout the specification.

Hereinbelow, exemplary embodiments of the present invention will be described in detail with reference to the accompanying drawings. The present invention, however, may be embodied in many alternate forms and should not be construed as limited to only the example embodiments set forth herein. Throughout the drawings, the same reference numerals will refer to the same or like parts.

Figure 2:
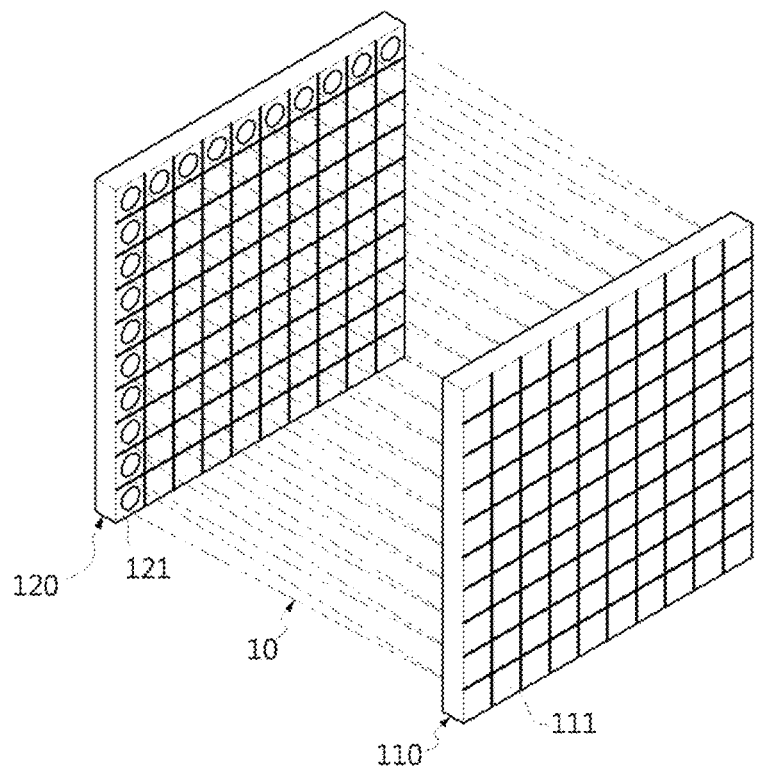
FIG. 2 is a schematic view showing an X-ray source and an X-ray detector of an X-ray radiograph device according to the present invention.

FIG. 2 is a schematic view showing an X-ray source 110 and an X-ray detector 120 of an X-ray radiograph device according to the present invention.

Referring to FIG. 2, the X-ray radiograph device according to an embodiment of the present invention may obtain a radiograph of a body, in particular, the device may be effectively used for dental clinics in which patient's head and mouth are used as a target, and include an X-ray source 110 and an X-ray detector 120.

The X-ray source 110 emits X-rays 10 and includes a plurality of X-ray emitting elements 111 that are arranged along a predetermined surface and respectively emit the X-rays 10. Each of the plurality of X-ray emitting elements 111 is an individual X-ray source. For example, the plurality of X-ray emitting elements 111 is configured to include respective cathodes and anodes.

Herein, it is preferable to use cathodes of field emission using nano-materials such as carbon nanotube (CNT), the cathodes of field emission using nano-materials solve the excessive power consumption problem caused by overheating of cathodes and also improve the focus limitation of an electron beam with a small size compared to a conventional thermal electron X-ray source.

The detailed configuration and driving method of the x-ray emitting elements 111 using such nano-materials are well known in the art, thus a detailed description is not provided.

It is preferable that the plurality of the X-ray emitting elements 111 is arranged in a matrix on a predetermined surface. In other words, each of the X-ray emitting elements 111 becomes a unit pixel of the X-ray source 110, is arranged in N rows and M columns according to the size of a target, and emits X-rays to the target. Herein, the predetermined surface may be a planar surface or a curved surface.

As a result, the X-ray source 110 including the X-ray emitting elements 111 arranged in a matrix configuration may emit an X-ray flux that transmits through a part or the entirety of a target, and the X-ray emitting elements 111 are arranged in an at least 2×2 matrix.

In addition, it is preferable to separately and respectively control the X-ray emitting elements 111. For example, an electrical switching means or a control program may drive the plurality of the X-ray emitting elements 111 at the same time, or, separately or sequentially drive the X-ray emitting elements 111 by a particular row or column.

The X-ray detector 120 detects the X-rays emitted from the X-ray source 110, and includes a plurality of X-ray detecting elements 121 that face the X-ray emitting elements 111 with the target being interposed therebetween. The plurality of X-ray detecting elements 121 generates electrical signals that are respectively proportional to an amount of incident X-rays on the X-ray detecting elements 121. In one embodiment, the X-ray detecting elements 121 may be image sensors.

In addition, the plurality of X-ray detecting elements 121 may be arranged in a matrix of N rows and M columns along a predetermined surface. The predetermined surface may be a planar surface or a curved surface.

The plurality of X-ray emitting elements 111 and the plurality X-ray detecting elements 121 are mapped one-to-one or one-to-many to each other. Therefore, the X-rays emitted from the X-ray emitting elements 111 are incident on at least one X-ray detecting element 121. It is preferable to arrange the X-ray detecting elements 121 in an at least 2×2 matrix.

Further, the X-ray detector 120 includes a signal processing part (not shown) that generates projection data about the target based on each electrical signals and positional information of the X-ray detecting elements 121.

In the X-ray radiography device according to the present invention described above, the X-ray emitting elements 111 of the X-ray source 110 are arranged in a pixel matrix configuration and emit the X-rays to the target, and the X-ray detecting elements 121 of the X-ray detector 120 are mapped one-to-one or one-to-many to the X-ray emitting elements 111 and detect the X-rays that transmitted through the target.

Therefore, an interior 2D projection image of the target may be obtained by image processing the projection data that are obtained based on each electrical signal and positional information of each X-ray detecting element 121. In addition, a 3D computed tomography image of the target may be obtained by reconstructing multi-directional projection data of the target.

In particular, in the X-ray radiography device according to the present invention, matrix configurations of the X-ray emitting elements 111 of the X-ray source 110 and the X-ray detecting elements 121 of the X-ray source 110 are adjusted such that X-ray fluxes that are respectively emitted from the X-ray emitting elements 111 and are transmitted through the target are maintained in parallel. Thus, the distance between the X-ray source 110 and the X-ray detector 120 may be minimized and the sizes of the X-ray source 110 and the X-ray detector 120 may also be minimized.

In this case, the X-rays detected by the X-ray detecting elements 121 of the X-ray detector 120 actually appear that the X-rays are focused on the X-ray detecting elements 121 in parallel, thus, the resolution of the image can be raised and image distortion such as penumbra can be remarkably reduced.

Herein, if necessary, in the X-ray radiography device according to the present invention, at least one collimator may be provided between the X-ray source 110 and the target and/or between the target and the X-ray detector 120 such that the X-ray emitting elements 111 and the X-ray detecting elements 121 are mapped one-to-one or one-to-many to each other. The collimator may have a grid configuration or a similar form.

Meanwhile, the X-ray emitting elements 111 and the X-ray detecting elements 121 of the X-ray radiography device according to the present invention may be arranged on separate planar surfaces or separate curved surfaces. In the following description, for convenience of explanation, the separate planar surfaces and the separate curved surfaces are separately described. Hereinafter, the embodiments of the present invention will be described with reference to fig.2 and other drawings.

First, the X-ray emitting elements 111 of the X-ray source 110 and the X-ray detecting elements 121 of the X-ray detector 120 of the X-ray radiography device according to the present invention are arranged on separate planar surfaces or on separate curved surfaces.

Figure 3:
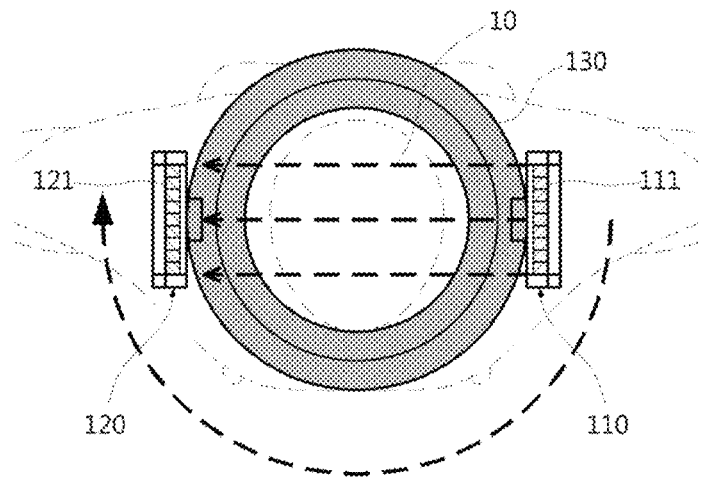
FIGS. 3 and 4 are a top-plan view and a perspective view of an X-ray radiography device according to a first embodiment of the present invention.
Figure 4:
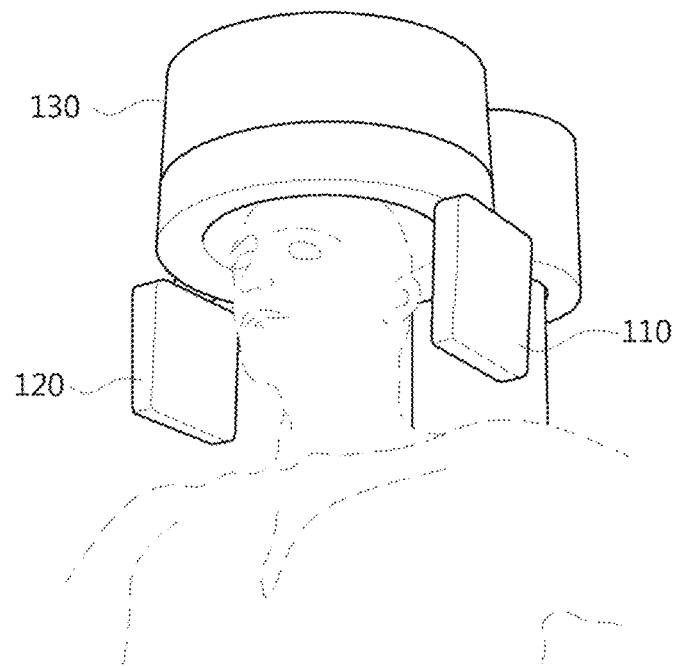

FIGS. 3 and 4 are a top-plan view and a perspective view of an X-ray radiography device according to a first embodiment of the present invention.

Referring to FIGS. 3 and 4, the X-ray radiography device according to the first embodiment of the present invention includes the X-ray source 110, the X-ray detector 120, and a housing 130. The X-ray emitting elements 111 of the X-ray source 110 and the X-ray detecting elements 121 of the X-ray detector 120 are arranged on separate planar surfaces or on separate curved surfaces, and the housing 130 provides an accommodation space for a target.

Herein, the housing 130 may be fixed on a supporter, or provided to be capable of moving across rows and having a cylindrical shape to encircle the target, for example, patient's head. Therefore, the height of the housing 130 may be adjusted according to an age or height of the target.

The X-ray source 110 and the X-ray detector 120 may be provided inside the housing 130, or may be provided on the bottom of the housing 130, as shown in the FIG. 4.

In addition, the X-ray source 110 and the X-ray detector 120 may rotate along the housing 130 with the target being interposed therebetween. Thus, a 2D projection image of the target is obtained by using the X-ray source 110 and the X-ray detector 120, and a 3D computed tomography image may be also obtained by obtaining and reconstructing multi-directional projection data of the target that are obtained by rotating the X-ray source 110 and the X-ray detector 120.

Meanwhile, the X-ray radiography device of FIGS. 3 and 4 is shown such that the X-ray source 110 and the X-ray detector 120 are arranged on separate planar surfaces, but the X-ray source 110 and the X-ray detector 120 may be arranged on separate curved surfaces, and each surface may cover the target.

Next, a 3D computed tomography image may be obtained by arranging the X-ray emitting elements 111 of the X-ray source 110 and the X-ray detecting elements 121 of the X-ray detector 120 of the present invention on separate planar surfaces or separate curved surfaces, and without moving or rotating at least one planer surface or curved surface.

Mode For Carrying Out The Invention

Figure 5A:
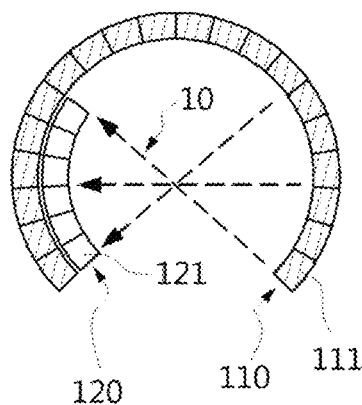
FIGS. 5a to 5c are views showing an X-ray radiography device according to a second embodiment of the present invention.
Figure 5B:
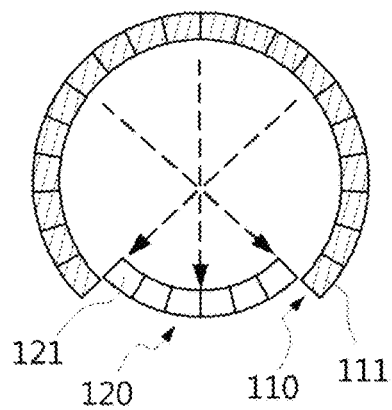
Figure 5C:
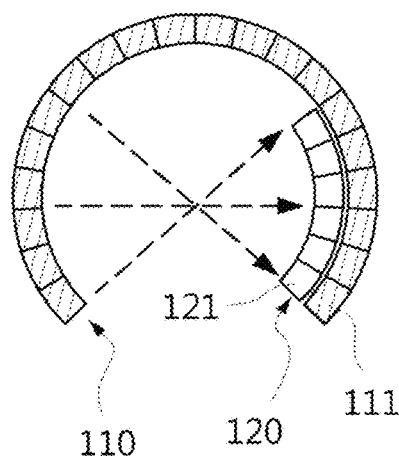

FIGS. 5a to 5c are views showing an X-ray radiography device according to a second embodiment of the present invention.

As can be seen in the figures, the X-ray radiography device according to the second embodiment of the present invention, the X-ray source 110 and the X-ray detector 120 are arranged on separate curved surfaces. A 3D computed tomography image may be obtained without moving or rotating the X-ray source 110 and the X-ray detector 120 while obtaining a 3D computed tomography image.

The surface of the X-ray source 110 has an arc-shaped cross-section which is perpendicular to a vertical axis of the target such that the surface covers at least three sides of the target. The plurality of X-ray emitting elements 111 that respectively emit X-rays are arranged in a matrix inside the X-ray source 110.

In addition, the X-ray detector 120 may move facing the target and a part of the X-ray source 110 while the X-ray detector 120 is interposed between the X-ray source 110 and the target, and the X-ray detecting elements 121 are arranged in a matrix inside the X-ray detector 120.

It is preferable to form an opening that is open to the outside on a part of the X-ray source 110. The opening may be used as a path for an entrance of the target. Further, the surface of the X-ray detector 120 may have a curved shape that corresponds to the inside of the X-ray source 110 and the radius thereof may be smaller than the X-ray source 110, and the surface of the X-ray detector 120 may move along the inside of the X-ray source 110.

In other words, in the X-ray radiography device according to the embodiment, the X-ray detector 120 is arranged inside the X-ray source 110 that has the arc shape and covers at least three sides of the target, and the X-ray detector 120 may move along the inside of the X-ray source 110.

As a result, a 2D projection image of the target may be obtained by the X-rays emitted from the X-ray emitting elements 111 that face the X-ray detector 120. Further, a 3D computed tomography image may be obtained without moving the X-ray source 110 by rotating the X-ray detector 120 and sequentially driving the X-ray emitting elements 111 that are facing the X-ray detector 120.

Meanwhile, contrary to the figures, the surface of the X-ray detector 120 may have an arc-shaped cross-section which is perpendicular to the vertical axis of the target such that the surface covers at least three sides of the target. A 2D projection image and a 3D computed tomography image may be identically obtained by moving the X-ray source 110 along the inside of the X-ray detector 120.

Next, a 2D projection image may be obtained even though the target has a small size, or a wide area is not secured, and the X-ray source 110 and the X-ray detector 120 are arranged on separate planar surfaces or on separate curved surfaces.

FIG. 6 is a view showing an X-ray radiography device according to a third embodiment of the present invention.

Referring to FIG. 6, in the X-ray radiography device according to the third embodiment of the present invention, the X-ray source 110 and the X-ray detector 120 are connected to each other by a flexible bending part 140, and the X-ray source 110 and the X-ray detector 120 are arranged on separate planar surfaces or on separate curved surfaces and connected to each other by the flexible bending part 140.

The X-ray radiography device according to the embodiment may obtain a 2D projection image of the target by properly bending the flexible bending part 140 such that the target is interposed between the X-ray source 110 and the X-ray detector 120 and receiving, by the X-ray detector 120, the X-rays emitted from the X-ray source 110 and having transmitted through the target.

In this case, the X-ray radiography device is useful when the target has a small size, or when it is difficult for the radiography device to secure a wide area. In one embodiment, in dental clinics, the X-ray radiography device is useful to radiograph multiple teeth that are inside the mouth. Thus, radiologists may easily perform the radiograph and patients may feel comfortable while radiographing.

In the following embodiment, the X-ray emitting elements 111 of X-ray source 110 and the X-ray detecting elements 121 of the X-ray detector 120 are arranged on a single planer surface or on a single curved surface.

First, FIGS. 7a and 7b, are schematic views of the X-ray source 110 and the X-ray detector 120 capable of being applied to fourth to sixth embodiments of the present invention, and schematically show arrangement configurations of the X-ray emitting elements 111 and the X-ray detecting elements 121.

Referring to FIG. 7a, the X-ray emitting elements 111 and the X-ray detecting elements 121 are arranged in a stripe matrix in which the X-ray emitting elements 111 and the X-ray detecting elements 121 are arranged in alternate columns or in alternate rows. Referring to FIG. 7b, the X-ray emitting elements 111 and the X-ray detecting elements 121 are arranged in a grid matrix in which the X-ray emitting elements 111 and the X-ray detecting elements 121 are alternately arranged in each column and each row of the grid matrix.

Figure 8A:
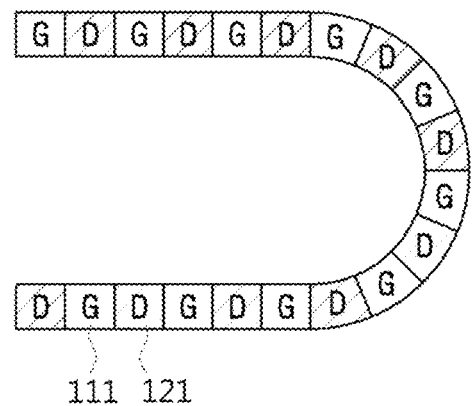

In succession, FIG. 8a shows a schematic view of the X-ray radiography device of the fourth embodiment of the present invention, and the X-ray emitting elements 111 and the X-ray detecting elements 121 are arranged along the single surface having flexibility. Herein, the X-ray emitting elements 111 and the X-ray detecting elements 121 are arranged in the matrix of FIG. 7a or 7b.

Therefore, the X-ray radiography device according to the embodiment of the present invention may obtain a 2D projection image of the target by properly bending the single surface such that the target is interposed between the X-ray source 110 and the X-ray detector 120, and receiving, by the X-ray detector 120, the X-rays emitted from the X-ray source 110 and transmitted through the target. Further, a 3D computed tomography image may be obtained by reconstructing multi-directional projection data that are obtained by rotating the X-ray source 110 and the X-ray detector 120 with the target being interposed therebetween.

Figure 8B:
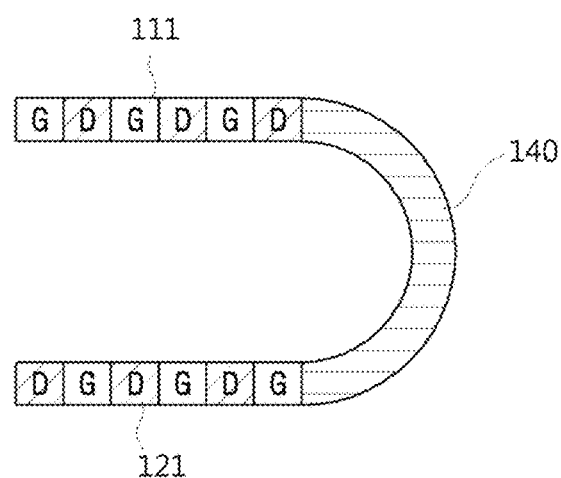

FIG. 8b shows a schematic view of the X-ray radiography device of the fourth embodiment of the present invention, two surfaces in which the X-ray emitting elements 111 and the X-ray detecting elements 121 are arranged on the surface are provided, the two surfaces are connected through the bending part 140 to face each other with the target being interposed therebetween. Herein, the X-ray emitting elements 111 and the X-ray detecting elements 121 are arranged on the two surfaces in the matrix of FIG. 7a or 7b.

In this case, the X-rays emitted from the X-ray emitting elements 111 of a first surface that is one of the two surfaces and having been transmitted through the target are detected by the X-ray detecting elements 121 of a second surface that is the other surface of the two surfaces, and the X-rays emitted from the X-ray emitting elements 111 of the second surface and having been transmitted through the target are detected by the X-ray detecting elements 121 of the first surface. Thus, a 2D projection image of the target may be obtained by using electrical signals and positional information of the X-ray detecting elements 121 of the first and second surfaces, and a 3D computed tomography image may be also obtained by reconstructing multi-directional data that are obtained by rotating the first and second surfaces with the target being interposed therebetween.

Figure 9:
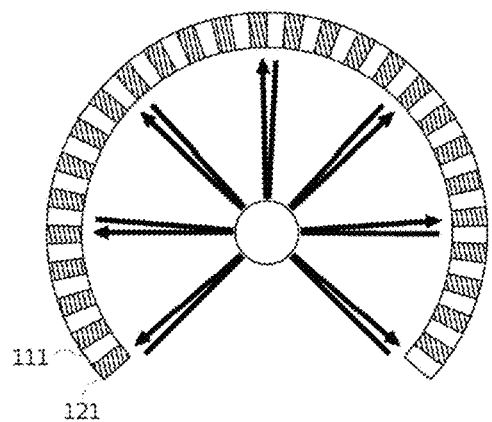
FIG. 9 is a schematic view of the X-ray source and the X-ray detector of an X-ray radiography device according to a fifth embodiment of the present invention.

FIG. 9 is a schematic view of the X-ray source and the X-ray detector of an X-ray radiography device according to a fifth embodiment of the present invention. The X-ray radiography device according to the fifth embodiment may obtain a 2D projection image and a 3D computed tomography image without rotating the X-ray source 110 and the X-ray detector 120 in which the X-ray emitting elements 111 of the X-ray source 110 and the X-ray detecting elements 121 of the X-ray detector 120 are arranged to cover at least three sides of the target.

Referring to FIG. 9, the X-ray emitting elements 111 and the X-ray detecting elements 121 are arranged on a single curved surface having a predetermined circumference.

Herein, the X-ray emitting elements 111 of the X-ray source 110 and the X-ray detecting elements 121 of the X-ray detector 120 may be arranged in a stripe matrix of FIG. 7a or a grid matrix of FIG. 7b. A 2D projection image may be obtained by detecting the X-rays, respectively emitted from the X-ray emitting elements 111 and having been transmitted through the target, by the X-ray detecting elements 121 that face the X-ray emitting elements 111.

In addition, multi-directional projection data are effectively obtained by detecting the X-rays emitted from the X-ray emitting elements 111 that are sequentially driven by a row or column through the X-ray detecting elements 121 facing the X-ray emitting elements 111, thus a 3D computed tomography image may be obtained without rotating the X-ray source 110 and the X-ray detector 120.

In particular, in this case, it is advantageous for obtaining X-ray image data by using a back scattering of the X-rays emitted from the plurality of X-ray emitting elements 111.

Figure 10:
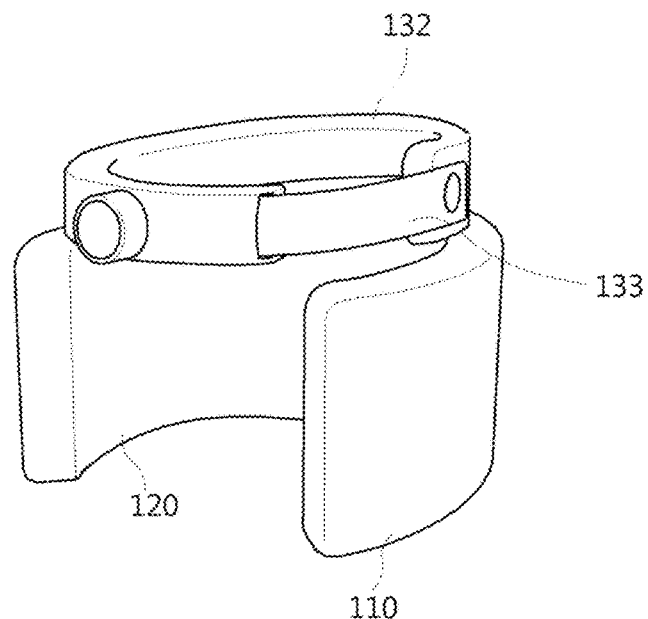
FIG. 10 is a view showing an X-ray radiography device according to a sixth embodiment of the present invention.

FIG. 10 is a view showing an X-ray radiography device according to a sixth embodiment of the present invention. In this embodiment, the X-ray emitting elements 111 of the X-ray source 110 and the X-ray detecting elements 121 of the X-ray detector 120 are arranged on a single planar surface or a curved surface. Compact design of the X-ray radiography device is achieved by reducing the size of the device. Meanwhile, the device may be portable by using a separate fixing part.

Referring to FIG. 10, in the X-ray radiography device according to the sixth embodiment of the present invention, the X-ray emitting elements 111 of the X-ray source 110 and the X-ray detecting elements 121 of the X-ray detector 120 are arranged on a single curved surface having a predetermined circumference. Herein, the X-ray emitting elements 111 and the X-ray detecting elements 121 may be arranged in a stripe matrix of FIG. 7a or in a grid matrix of FIG. 7b, and the single surface may be provided in a separate casing.

The single curved surface, on which the X-ray emitting elements 111 of the X-ray source 110 and the X-ray detecting elements 121 of the X-ray detector 120 are arranged, is coupled to a fixing part 132 that is fixed on the head or the body of the target. Herein, the fixing part 132 provides a predetermined space part that accommodates the target, and includes an adjusting means 133 that is capable of adjusting the space part.

Herein, the X-ray radiography device according to the sixth embodiment may have a compact size to be easily carried, obtain a 2D projection image by fixing the fixing part 132 to the target such as head, arm, leg, etc. and obtain a 3D computed tomography image without rotating the X-ray source 110 and the X-ray detector 120.

Meanwhile, in the X-ray radiography device according to the present invention, the X-ray emitting elements 111 and the X-ray detecting elements 121 may be mapped one-to-one or one-to-many to each other. In case of the one-to-many mapping, a 3D computed tomography image may be obtained by individually controlling the X-ray emitting elements 111 and by irradiating the X-rays in multiple directions toward the target.

Figure 11:
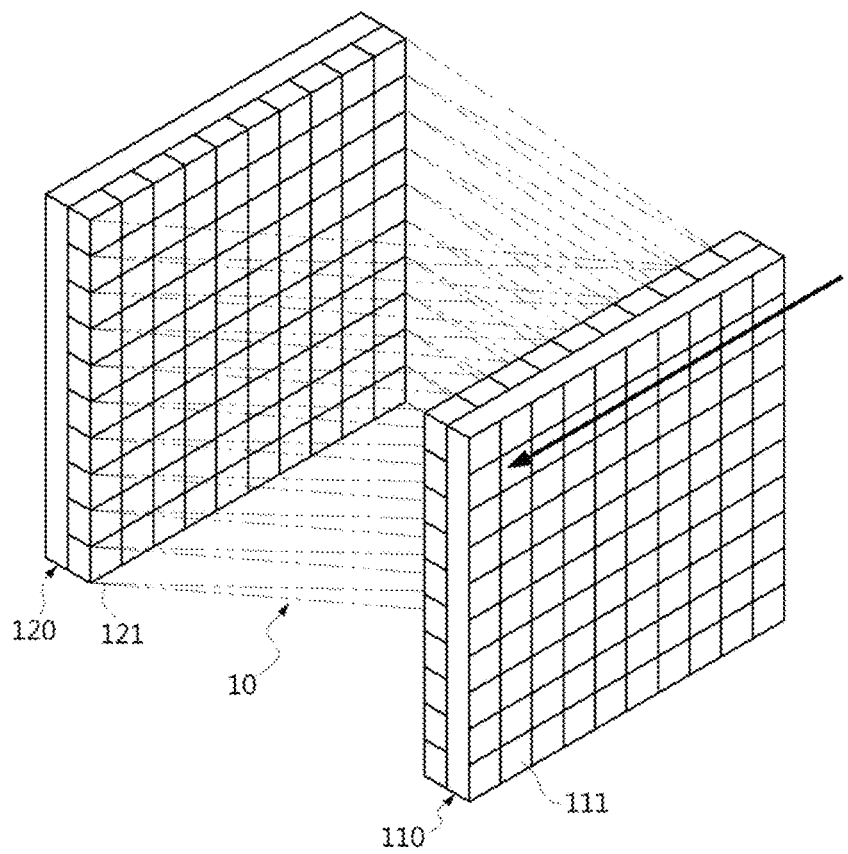
FIG. 11 is a schematic view of the X-ray source and the X-ray detector of an X-ray radiography device according to a seventh embodiment of the present invention.

FIG. 11 is a schematic view of the X-ray source and the X-ray detector of an X-ray radiography device according to a seventh embodiment of the present invention.

Referring to FIG. 11, the X-ray radiography device according to the seventh embodiment of the present invention is externally similar to the embodiment of FIG. 2. However, in the seventh embodiment, the X-ray emitting elements 111 of the X-ray source 110 are mapped one-to-many to the X-ray detecting elements 121 of the X-ray detector 120.

In other words, the X-ray emitting elements 111 sequentially irradiate X-rays while the X-ray emitting elements 111 of the X-ray source 110 are mapped one-to-many to the X-ray detecting elements 121 of the X-ray detector 120. Herein, it is preferable to configure the X-ray emitting elements 111 such that at least one row or column of the X-ray emitting elements 111 may be mapped to all of the X-ray detecting elements 121 and sequentially irradiate the X-rays toward the target.

Accordingly, the X-ray detector 120 detects the X-rays having been transmitted through the target in different directions and obtains multi-directional X-ray detecting results. Thus, a 3D computed tomography image may be obtained by reconstructing projection data that are obtained by X-ray detection results in each direction.

In addition, the seventh embodiment may be applied the other embodiments described above. A 3D computed tomography image may be obtained without rotating the X-ray source 110 and/or the X-ray detector 120, or by rotating the X-ray source 110 and/or the X-ray detector 120 at a minimum angle.

Reference will now be made in greater detail to an exemplary embodiment of the present invention, an example of which is illustrated in the accompanying drawings. Wherever possible, the same reference numerals will be used throughout the drawings and the description to refer to the same or like parts.

INDUSTRIAL APPLICABILITY

The present invention may be applied to an X-ray radiography device that captures radiographs of patient's body.

The invention claimed is:

1. An X-ray radiography device, the device comprising:
an X-ray source including a plurality of X-ray emitting elements arranged in an at least 2×2 pixel matrix and respectively emitting X-rays to a target; and
an X-ray detector detecting the X-rays transmitted through the target
wherein one of the X-ray source and the X-ray detector has a curved surface surrounding the target,
wherein the X-ray detector includes a plurality of X-ray detecting elements arranged in an at least 2×2 pixel matrix on a planar surface or a curved surface to be mapped one-to-one or one-to-many to the X-ray emitting elements, and respectively to detect each of the X-rays transmitted through the target,
wherein the plurality of X-ray emitting elements and the plurality of X-ray detecting elements are arranged on separate planar surfaces or on separate curved surfaces, and
wherein the X-ray radiography device comprise a flexible bending part connecting the separate planar surfaces or the separate curved surfaces to each other.

2. The X-ray radiography device of claim 1, wherein the X-ray emitting elements include cathodes of carbon nanotubes.

3. The X-ray radiography device of claim 1, wherein the X-ray emitting elements and the X-ray detecting elements are arranged to face each other with the target being interposed between the X-ray emitting elements and the X-ray detecting elements.

4. The X-ray radiography device of claim 1, when the plurality of X-ray emitting elements are arranged along the curved surface, i) the arrangement of the plurality of X-ray emitting elements is perpendicular to a vertical axis of the target and covers at least three sides of the target, and ii) the plurality of X-ray detecting elements move between the target and the plurality of X-ray emitting elements while facing the target, and
when the plurality of X-ray detecting elements are arranged along the curved surface, iii) the arrangement of the plurality of X-ray detecting elements is perpendicular to a vertical axis of the target and covers at least three sides of the target, and iv) the plurality of X-ray emitting elements move between the target and the plurality of X-ray detecting elements while facing the target.

5. The X-ray radiography device of claim 1, wherein the X-ray emitting elements and the X-ray detecting elements are arranged on a same planar surface or a same curved surface.

6. The X-ray radiography device of claim 5, wherein the X-ray emitting elements and the X-ray detecting elements are arranged in a grid matrix to alternately dispose the X-ray emitting elements and the X-ray detecting elements in each column and each row, or in a stripe matrix to respectively dispose the X-ray emitting elements and the X-ray detecting elements in alternate columns or in alternate rows.

7. The X-ray radiography device of claim 6, wherein the planar surface or the curved surface has flexibility.

8. The X-ray radiography device of claim 1, wherein the X-ray emitting elements sequentially emit the X-rays in a row or a column.

9. The X-ray radiography device of claim 1, wherein the curved surface defines an opening for the target.

10. An X-ray radiography device comprising:
a plurality of X-ray elements arranged on a lane, said X-ray elements configured to emit X-rays be selectively activated; and
a plurality of X-ray detecting elements configured to detect the X-rays transmitted,
wherein the X-ray detecting elements are arranged on the plane where the X-ray emitting elements are arranged,
wherein the X-ray detector includes a plurality of X-ray detecting elements arranged in an at least 2×2 pixel matrix on a planar surface or a curved surface to be mapped one-to-one or one-to-many to the X-ray emitting elements, and respectively to detect each of the X-rays transmitted from the X-ray emitting elements, and
wherein the plurality of X-ray emitting elements and the plurality of X-ray detecting elements are arranged on separate planar surfaces or on separate curved surfaces.
wherein the X-ray radiography device comprise a flexible bending part connecting the separate planar surfaces or the separate curved surfaces to each other.

11. The X-ray radiography device of claim 10, wherein the plurality of X-ray emitting elements and the plurality of X-ray detecting elements are alternately arranged in a stripe form.

12. The X-ray radiography device of claim 10, wherein the plurality of X-ray emitting elements and the plurality of X-ray detecting elements are alternately arranged in a grid form.

13. The X-ray radiography device of claim 10, wherein the plane is a curved to surround the target.

* * * * *